(12) United States Patent
Kim (10) Patent No.: US 12,419,651 B2
(45) Date of Patent: Sep. 23, 2025

(54) CONDENSING SCREW FOR IMPLANT PROCEDURE HAVING DOUBLE SPIRAL STRUCTURE

(71) Applicant: HAENAEM CO., LTD., Pyeongtaek-si (KR)

(72) Inventor: Sung Ju Kim, Pyeongtaek-si (KR)

(73) Assignee: HAENAEM CO., LTD. (KR)

( * ) Notice: Subject to any disclaimer, the term of this patent is extended or adjusted under 35 U.S.C. 154(b) by 908 days.

(21) Appl. No.: 17/631,448

(22) PCT Filed: Nov. 18, 2019

(86) PCT No.: PCT/KR2019/015721
§ 371 (c)(1),
(2) Date: Jun. 11, 2022

(87) PCT Pub. No.: WO2021/020656
PCT Pub. Date: Feb. 4, 2021

(65) Prior Publication Data
US 2023/0301696 A1    Sep. 28, 2023

(30) Foreign Application Priority Data
Jul. 30, 2019  (KR) ........................ 10-2019-0092685

(51) Int. Cl.
*A61B 17/16* (2006.01)
*A61C 8/00* (2006.01)

(52) U.S. Cl.
CPC ...... *A61B 17/1655* (2013.01); *A61B 17/1615* (2013.01); *A61B 17/1673* (2013.01); *A61B 17/1688* (2013.01); *A61C 8/0018* (2013.01)

(58) Field of Classification Search
CPC ............ A61B 17/1615; A61B 17/1655; A61B 17/1673; A61B 17/1688
See application file for complete search history.

(56) References Cited

U.S. PATENT DOCUMENTS

| 6,382,976 B1 | 5/2002 | Wagner | |
| 12,220,297 B2* | 2/2025 | Huwais | A61B 17/1615 |
| 2009/0136898 A1* | 5/2009 | Kim | A61C 8/0092 |
| | | | 433/165 |

(Continued)

FOREIGN PATENT DOCUMENTS

| EP | 1578299 B1 | 2/2012 |
| KR | 10-1276418 B1 | 6/2013 |

(Continued)

*Primary Examiner* — Nicholas W Woodall (57) ABSTRACT

Disclosed herein is a "condensing screw for an implant procedure." A "condensing screw for an implant procedure" of the present invention is provided with: a screw main body which is inserted into an implant planting hole formed by an pilot drilling process, enlarges the implant planting hole to a size large enough to insert an implant fixture, and forms osseodensification regions on the side surfaces and the inside of the implant planting hole; and a shank which extends upward from the screw main body, is coupled to a driving unit, and transmits the torque of the driving unit to the screw main body. The condensing screw can enlarge the implant planting hole and perform the osseodensification process simultaneously, and can be used for maxillary sinus augmentation.

5 Claims, 9 Drawing Sheets

(56) References Cited

U.S. PATENT DOCUMENTS

| | | | |
|---|---|---|---|
| 2012/0244497 A1* | 9/2012 | Huwais | A61C 8/0089 |
| | | | 433/165 |
| 2015/0297275 A1* | 10/2015 | Huwais | A61B 17/863 |
| | | | 606/315 |
| 2015/0297321 A1 | 10/2015 | Chen | |
| 2019/0029695 A1* | 1/2019 | Huwais | A61B 17/1673 |
| 2020/0155210 A1* | 5/2020 | Huwais | A61B 17/7035 |
| 2022/0047359 A1* | 2/2022 | Huwais | A61C 8/0069 |
| 2024/0398516 A1* | 12/2024 | Hernández Suarez | |
| | | | A61C 8/0089 |

FOREIGN PATENT DOCUMENTS

| KR | 10-2015-0123494 A | 11/2015 |
|---|---|---|
| KR | 10-2016-0124790 A | 10/2016 |

\* cited by examiner

CONDENSING SCREW FOR IMPLANT PROCEDURE HAVING DOUBLE SPIRAL STRUCTURE

TECHNICAL FIELD

The present invention relates to a condensing screw for implant surgery, and more particularly, to a condensing screw for implant surgery having double spiral structure, which can simultaneously perform expansion of an implant planting hole and osseodensification using a double spiral structure.

BACKGROUND ART

Dental implants are used to secure other dental articles in the oral cavity and the prosthesis received in the oral cavity. One of important purposes of the implant treatment is to firmly secure a screw made of a biologically suitable material to the lower jaw bone or the maxillary bone with durability.

In general, two maxillary sinuses are located at the upper side of the roots of the molar teeth, and are empty cavities surrounded by bones. Accordingly, when a molar tooth located on the maxillary sinus is extracted, it is difficult to perform a normal implant surgery due to the lack of the amount of bone of the maxillary sinus.

In this case, it is possible to plant an implant through surgery using an artificial bone. In other words, when a graft bone is implanted in the maxillary bone, physical properties of the graft bone of a powder type is changed into a hard bone so that the maxillary bone has a thickness capable of allowing implant placement.

Here, a membrane exists between the empty space of the maxillary sinus and the skull. The membrane approaches the maxillary sinus, and it acts as a cause of making implant surgery difficult when an implant is planted.

That is, the membrane in the maxillary sinus can be easily torn when the blade of the drill comes into contact with the membrane or when a surgical operator instantaneously applies an excessive force while the drill is rotated during drilling of the maxillary sinus. If the membrane is torn, it may cause infection of the maxillary sinus. So, an operator needs to be always careful not to tear the maxillary sinus.

Therefore, recently, the operator plants an implant through a complex process of drilling once with a pilot drill, expanding the size of a hole by drilling with a drill with a thicker bit, and inserting an implant suitable for the size of the hole.

However, in order to plant an implant stably, since osseodensification is required, an osseodensification process must be performed using a bur.

Figure 1:
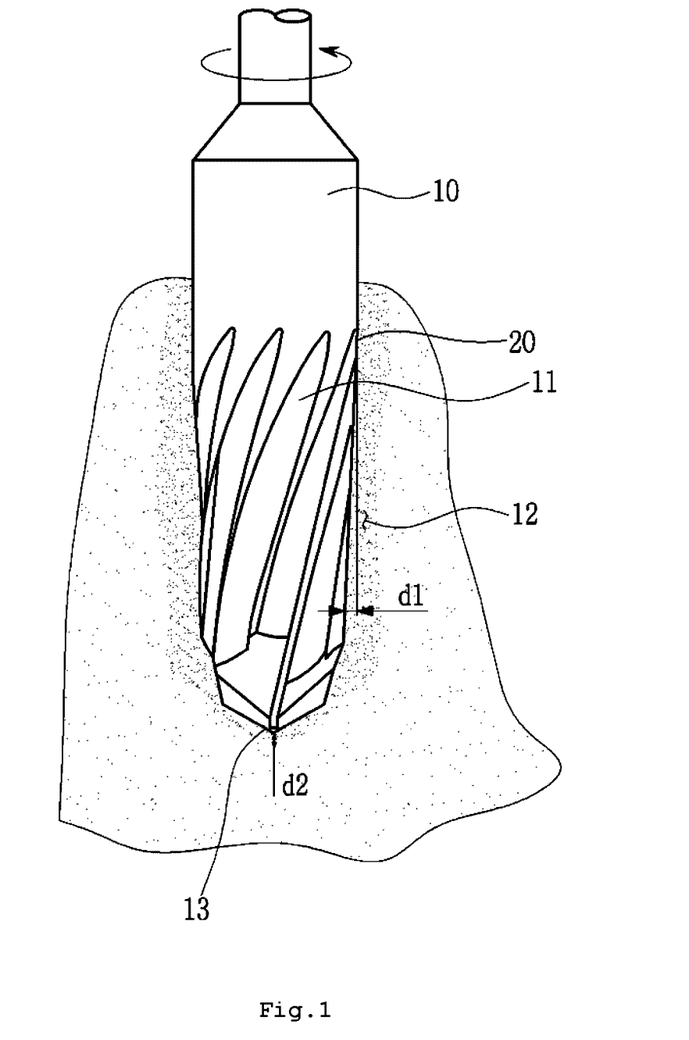
FIG. 1 is a view illustrating an osseodensification process using a burr according to a conventional art.

FIG. 1 is a cross-sectional view illustrating a process of performing osseodensification using a conventional burr 10. As illustrated in the drawing, the conventional burr 10 includes a thread 11 formed on the surface thereof in the opposite direction to a rotational direction of the burr 10.

When the burr 10 is rotated, the thread 11 is formed in the opposite direction to the rotational direction of the burr 10 so that the bone powder separated from the inner wall surface of an implant planting hole 20 is not discharged to the outside and is pressed and compressed toward the inner wall surface of the implant planting hole 20.

Therefore, without using the drill, the implant planting hole 20 can be pressurized and expanded without any removal of the bone. However, the conventional burr 10 has excellent pressing force since the thread 11 presses the inner wall surface of the implant planting hole 20 at the time of rotation, but pressing force toward the inside (the lower part of the drawing) of the implant planting hole 20 is relatively weak.

Thus, since the thickness (D2) of an inner osseodensification region 13 formed inside the implant planting hole 20 is smaller than the thickness (D1) of a lateral osseodensification region 12 formed on the inner wall surface of the implant planting hole 20, there is a limitation in that it is not sufficient to be used for maxillary sinus lift.

In addition, since the implant planting hole 20 is expanded by pressing without the removal of the bone, a significant degree of pressure is applied to the lateral side of the implant planting hole 20 so that a patient feels a lot of pain.

DISCLOSURE

Technical Problem

Accordingly, the present invention has been made in view of the above-mentioned problems occurring in the prior art, and it is an object of the present invention to provide a condensing screw for implant surgery, capable of being used for bone expansion and for maxillary sinus lift by simultaneously pressing an implant planting hole in a lateral direction and in an upward direction.

It is another object of the present invention to provide a condensing screw for implant surgery, capable of doubling the effect of maxillary sinus lift by performing osseodensification together.

It is a further object of the present invention to provide a condensing screw for implant surgery, capable of preventing a damage of a membrane during a maxillary sinus lift procedure.

It is a still further object of the present invention to provide a condensing screw for an implant operation, capable of minimizing a patient's burden by reducing a process for planting an implant and distributing pressure applied to a lateral side.

Technical Solution

To accomplish the above object, there is provided a condensing screw for implant surgery including: a screw main body which is inserted into an implant planting hole formed by a pilot drill to enlarge the implant planting hole to a size that an implant fixture can be inserted into the implant planting hole, and which forms osseodensification regions on the lateral surface and the inside of the implant planting hole; and a shank extending from the upper part of the screw main body to be coupled to a driving unit and transmitting rotational force of the driving unit to the screw main body.

Here, the screw main body includes: a compression screw thread part spirally formed on the surface of the screw main body in the opposite direction to a rotational direction of the screw main body to provide cutting force in the insertion direction when the screw main body is rotated, and compressing bone powder by laterally pressing the inner wall surface of an implant planting hole; and a plurality of bone powder guide grooves formed to be spirally recessed in the opposite direction to the rotational direction of the screw main body at regular intervals along the outer circumference of the screw main body to the upper part from the lower part of the screw main body in order to guide the bone powder separated from the inner wall surface of the implant planting hole and water supplied from the outside to the lower part of the screw main body by cutting force of the compression screw thread part.

Advantageous Effects

As described above, the condensing screw for implant surgery according to the present invention has the compression screw thread part formed in the opposite direction to the rotational direction of the screw main body, and the bone powder guide groove formed between the compression screw thread parts to be overlapped.

The compression screw thread part is provided to perform expansion through cutting by getting in contact with the inner wall surface of the implant planting hole to press the inner wall surface of the implant planting hole when the screw main body is rotated and to perform osseodensification by laterally pressing the bone powder generated during cutting.

At the same time, the bone powder is supplied to the lower compression dome of the screw main body through the bone powder guide groove to form an osseodensification process region inside the implant planting hole. So, the membrane can be lifted without damaging the membrane of the maxillary sinus. In addition, the osseodensification process region is formed at the lower portion of the membrane, thereby enabling implant placement without an additional osseodensification process.

The conventional method performs processes of drilling using a number of drills to gradually increase the diameter after drilling using the pilot drill to plant the conventional implant, performing osseodensification process if necessary, performing final drilling, and planting an implant. However, the condensing screw according to the present invention can simultaneously perform drilling a hole using the pilot drill, expansion and osseodensification process using the condensing screw, thereby shortening a process of implant placement.

Therefore, the condensing screw according to the present invention allows an operator to perform implant surgery more easily and makes the surgery process safe since making the implant surgery process simpler than the conventional implant placement method.

Moreover, since the implant placement process is shortened, the burden of the operator can be reduced.

EXPLANATION OF REFERENCE NUMERALS

100: Condensing screw 110: Screw main body
111: Compression screw thread part 112: Thread
112a: Cutting blade 112b: Densification surface
113: Valley 115: Bone powder guide groove
117: Lower compression dome 117a: Guide groove connection groove
117b: Guide curved surface 117c: Vertical surface
120: Shank 121: Connector
200: water supply member 210: Driving unit
220: pilot drill 300: Implant planting hole
330: lateral osseodensification region 340: upper osseodensification region

MODE FOR INVENTION

Hereinafter, preferred embodiments of the present invention will now be described in detail with reference to the attached drawings, in which like reference numbers denote like components throughout the drawings.

The terms "comprising" and "including" in the discussion directed to the present invention and the claims are used in an open-ended fashion and thus should be interrupted to mean "including", but not limited thereto.

Hereinafter, specific embodiments in which a condensing screw for implant surgery of the present invention will be described.

Figure 2:
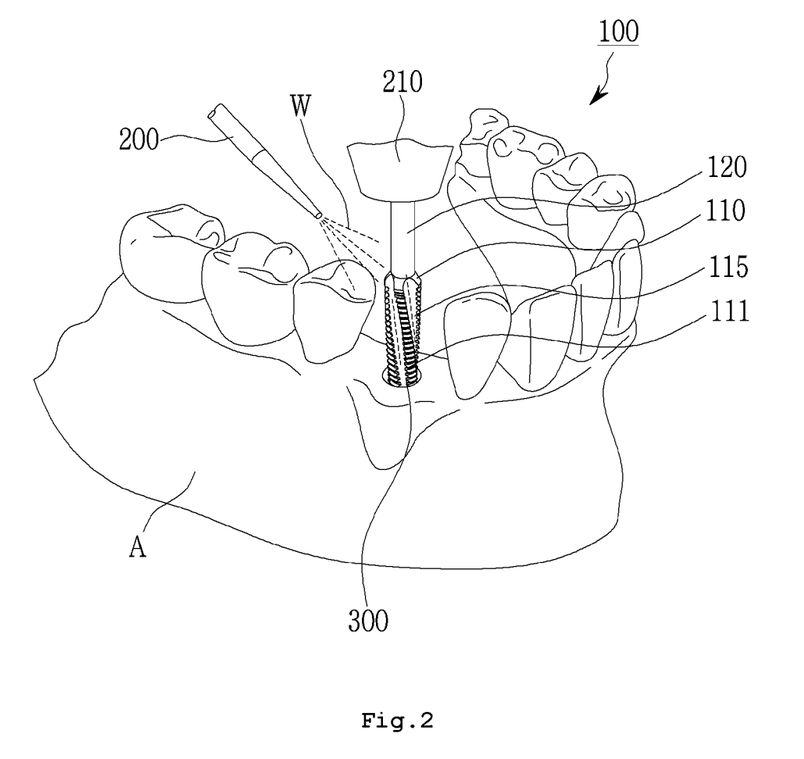
FIG. 2 is a view illustrating an implant planting hole expansion process using a condensing screw according to an embodiment of the present invention.
Figure 3:
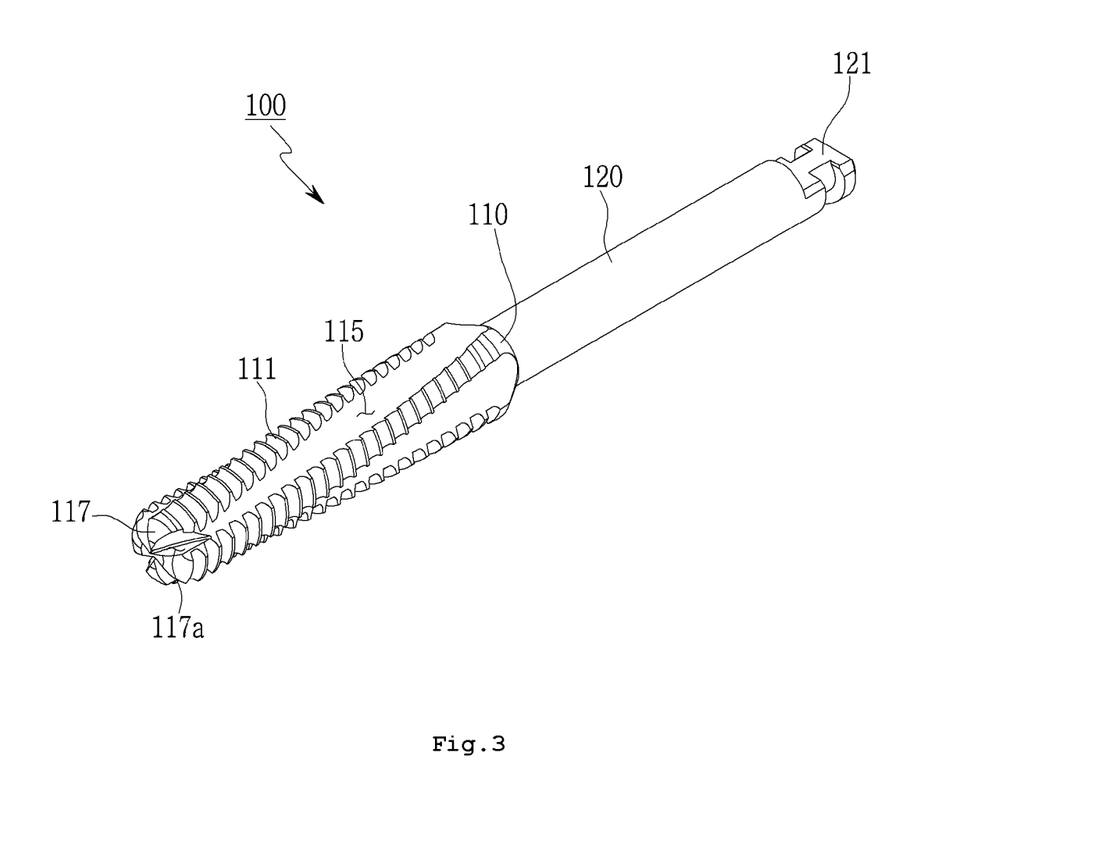
FIG. 3 is a perspective view illustrating the condensing screw according to the embodiment of the present invention.

FIG. 2 is a view illustrating a process of expanding an implant planting hole of a mandible molar region (A) using a condensing screw 100 according to an embodiment of the present invention, and FIG. 3 is a perspective view illustrating the condensing screw 100 according to the embodiment of the present invention.

The condensing screw 100 of the present invention can perform hole expansion by simultaneously pressing an implant planting hole 300 formed by a pilot drill in a lateral direction and in an inward direction without removing a bone. In addition, the condensing screw 100 of the present invention compresses the bone powder, which is generated in the process of expanding the implant planting hole, in the lateral direction and in the inward direction so as to form an osseodensification region on the lateral side and to stably form another osseodensification region on the inner side.

The condensing screw 100 according to the present invention can be used for maxillary sinus lift and for osseointegration.

As illustrated in FIG. 2, the condensing screw 100 of the present invention includes: a screw main body 110 inserted into the implant planting hole 300 formed by the pilot drill; and a shank 120 extending from the upper part of the screw main body 110 and coupled to a driving unit 210.

A connector 121 coupled to the driving unit 210 is provided at an end portion of the shank 120. The shank 120 is coupled to a driving unit 210, such as a driving motor, to transfer rotational force of the driving unit 210 to the screw main body 110. Accordingly, the screw main body 110 can be inserted into the implant planting hole 300 while rotating.

The screw main body 110 has a length and a diameter corresponding to a fixture (not shown) of an implant (not shown) so that the fixture (not shown) can be inserted into the screw main body 110. The screw main body 110 is inserted into the implant planting hole 300 and expands at a time to a size in which the fixture (not shown) can be inserted. Therefore, the entire work process can be greatly reduced, and an operator's burden and pain can be reduced.

Figure 4:
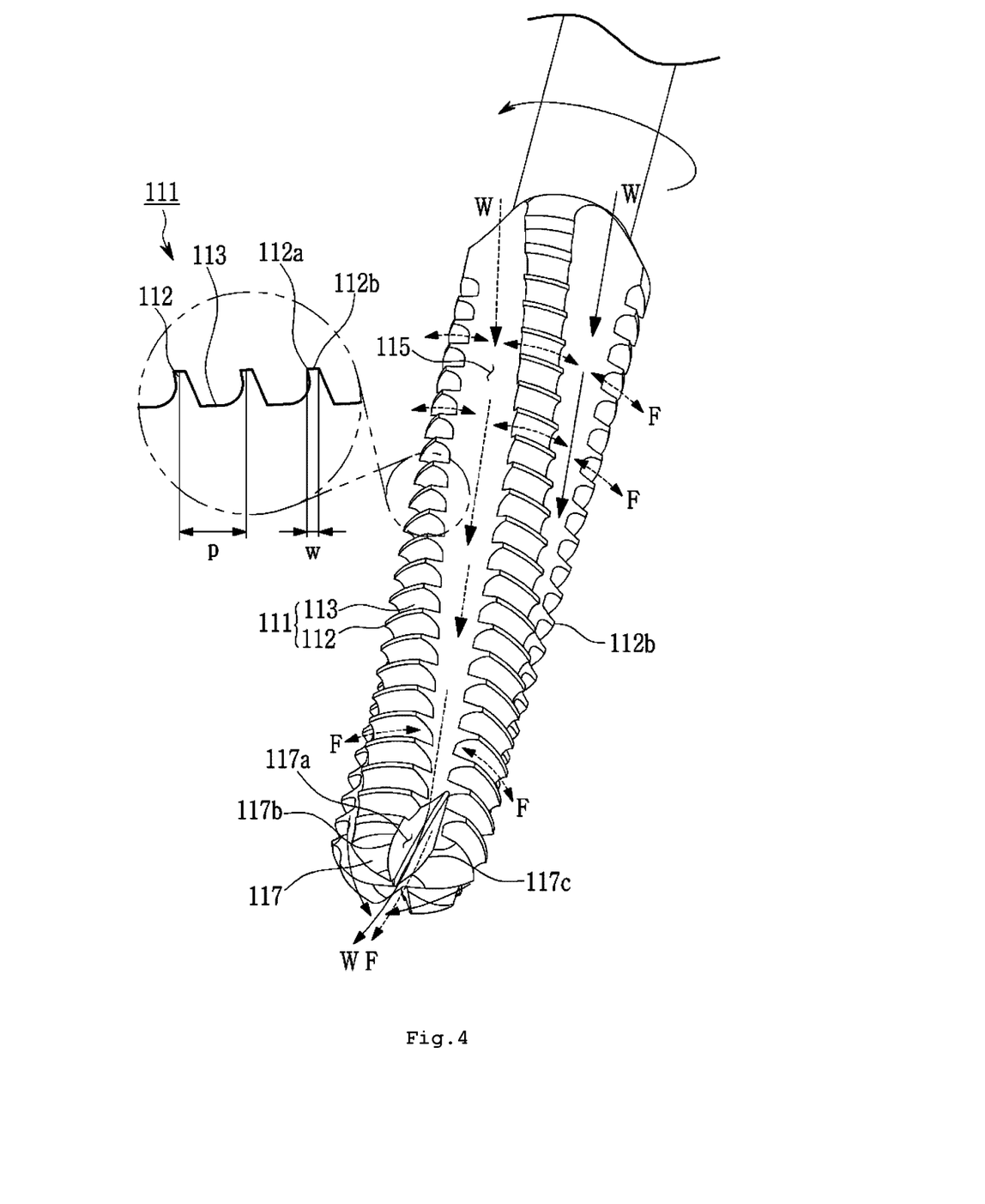
FIG. 4 is a perspective view of a main body of the condensing screw according to the embodiment of the present invention.
Figure 5:
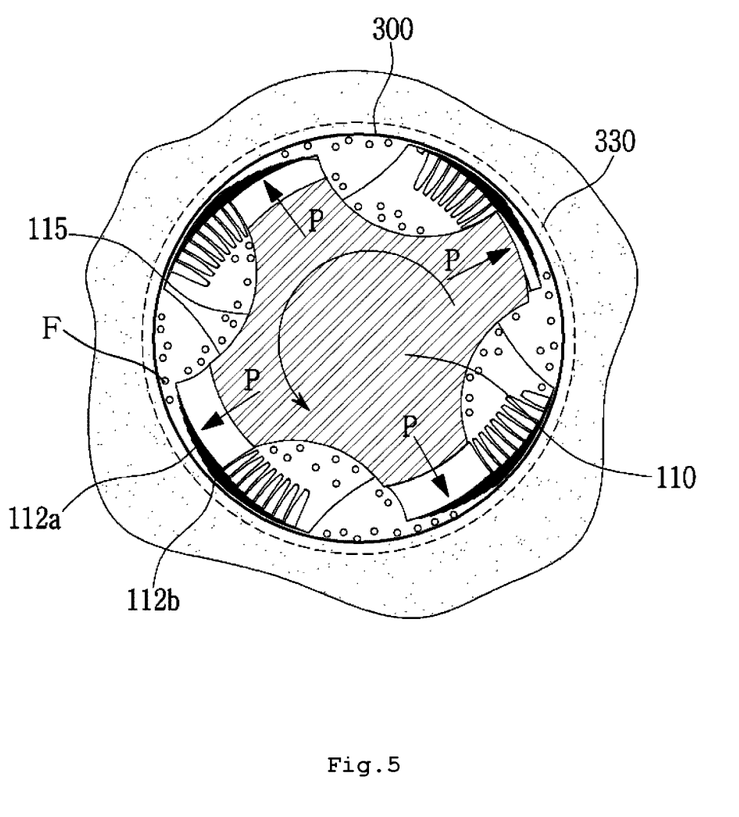
FIG. 5 is a cross-sectional view illustrating an osseodensification process of an implant planting hole by the condensing screw according to the embodiment of the present invention.

FIG. 4 is a perspective view of the screw main body 110, and FIG. 5 is a cross-sectional view illustrating a process in which the screw main body 110 is inserted into the inner wall surface of the implant planting hole 300 and perform osseodensification while rotating.

The screw main body 110 is formed such that the diameter of the screw main body 110 gradually decreases to the bottom from the top combined with the shank 120. The screw main body 110 includes: a compression screw thread part 111 spirally formed on the outer circumferential surface of the screw main body 110 in a longitudinal direction to expand the implant planting hole 300 and to perform osseodensification by compressing bone powder in the lateral direction; and a plurality of bone powder guide grooves 115 formed to be spirally recessed between the compression screw thread part 111 along the lower part from the upper part of the screw main body 110 to transfer the bone powder (F) and water (W) downwards to perform osseodensification on the lower part.

Furthermore, a lower compression dome 117 for compressing the bone powder (F) guided by the bone powder guide grooves 115 is provided at the lower part of the screw main body 110.

The compression screw thread part 111 is formed in the spiral direction opposed to the rotational direction of the screw main body 110. The compression screw thread portion 111 is formed in a shape in which a plurality of threads 112 and a plurality of valleys 113 are repeated. That is, as illustrated in FIG. 4, when the screw main body 110 is rotated in the clockwise direction, the compression screw thread portion 111 is formed in a spiral shape in the counterclockwise direction.

A cutting blade 112a is formed at the front end of each thread 112, and an upper part of the thread 112 has a densification surface 112b having a predetermined area.

When the operator drives the driving unit 210 to insert the screw main body 110 into the implant planting hole 300, the thread 112 of the compression screw thread unit 111 gets in contact with the inner wall surface of the implant planting hole 300 by insertion pressure and rotational force of the screw main body 110 and applies pressure. In this instance, as illustrated in FIG. 5, the cutting blade 112a located at the front end of the thread 112 first gets in contact with the inner wall surface of the implant planting hole 300 and cuts a predetermined part of the implant planting hole 300.

Because being formed in the opposite direction to the rotational direction of the screw main body 110, the cutting blade 112a can perform minute cutting.

The bone powder (F) separated from the inner wall surface of the implant planting hole 300 by cutting of the cutting blade 112a is moved through the valley 113 to be moved in the lateral direction of the implant planting hole 300. At this time, water (W) is supplied by a water supply member 200 (See FIG. 2), so that the bone powder (F) stirred together with the water (W) is directed to the inner wall surface of the implant planting hole 300.

After the cutting blade 112a gets in contact with the inner wall surface of the implant planting hole 300, the densification surface 112b comes in surface contact with the inner wall surface of the implant planting hole 300 and compresses the bone powder (F) and the water moved through the valley 113 toward the inner wall surface of the implant planting hole 300. The water and the bone powder (F) are stirred and pressed against the inner wall surface of the implant planting hole 300 by pressure (P) of the densification surface 112b, thereby forming a lateral osseodensification region 330.

Here, the condensing screw 100 of the present invention increases the effect of osseodensification as a contact area between the densification surface 112b, which is formed on the thread 112, and the inner wall surface of the implant planting hole 300 gets wider. So, the compression screw thread part 111 has a small a lead angle, a pitch (p) between the thread 112 and the thread 112 is formed to be narrow, and a width (W) of the densification surface 112b is preferably formed to be wide.

If the lead angle of the compression screw thread part 111 is large, the efficiency of cutting the inner wall surface of the implant planting hole 300 can be improved, but the number of the threads 112 and the valleys 113 formed on the entire screw main body 110 is reduced, thereby reducing the contact area.

The bone powder guide groove 115 supplies water (W) and bone powder (F) to the lower part from the upper part of the screw main body 110. The plurality of bone powder guide grooves 115 are formed to be spirally recessed in a spiral direction at predetermined angle intervals along the outer circumference of the screw main body 110 downwards from the top of the screw main body 110. The bone powder guide groove 115 is also spirally formed in the opposite direction to the rotational direction of the screw main body 110 in the same manner as the compression screw thread portion 111.

A depth of the bone powder guide groove 115 is formed to be equal from the upper part to the lower part, and a width thereof becomes gradually narrower from the upper part to the lower part.

In this instance, the pitch of the bone powder guide groove 115 corresponds to two to three times the entire length of the screw main body 110, and the lead angle of the bone powder guide groove 115 is formed to be in the range from 60 degrees to 80 degrees. Accordingly, the plurality of bone powder guide grooves 115 are independently formed without being connected to each other throughout the screw main body 110.

Four bone powder guide grooves 115 according to the embodiment of the present invention are formed at 90 degree intervals in the circumferential direction, but this is just one example, and the number of the bone powder guide grooves 115 can be two to eight in the circumferential direction.

The lead angle of the bone powder guide groove 115 is formed to still larger than that of the compression screw thread part 111 so that the bone powder guide groove 115 is recessed from the upper part to the lower direction on the outer circumferential surface of the screw main body 110. Accordingly, the bone powder guide grooves 115 are formed to overlap between the compression screw thread part 111 formed on the outer circumferential surface of the screw main body 110 with a close pitch. That is, the plurality of bone powder guide grooves 115 and the plurality of compression screw thread parts 111 are formed to overlap in a double spiral shape.

The plurality of bone powder guide grooves 115 are formed to communicate with the valleys 113 of the compression screw thread portion 111. Accordingly, as illustrated in FIGS. 4 and 5, when the screw main body 110 is rotated, a portion of the bone powder (F) moved through the valley 113 is supplied to the bone powder guide groove 115 after the cutting blade 112 gets in contact with the inner wall surface of the implant planting hole 300.

The bone powder guide groove 115 serves to guide the water (W) supplied from the upper part and the bone power (F) supplied from the upper part to the lower part of the screw main body 110. The bone powder guide groove 115 extends from the upper part of the screw main body 110 to the lower part, thereby distributing water supplied from the upper part to each valley 113 and simultaneously guiding the water supplied from the upper part to the lower part of the screw main body 110. Additionally, bone powder guide groove 115 guides the bone powder (F), which is supplied from the plurality of valleys 113 formed in the longitudinal direction, to the lower part of the screw main body 110.

The bone powder (F) guided by the bone powder guide groove 115 is compressed toward the inside of the implant planting hole 300 (the lower part of the implant planting hole in the case of the mandible molar region, and the upper part of the implant planting hole I the case of the maxillary molar teeth), and can provide sufficient osseodensification to the inside of the implant planting hole 300 as well as the lateral wall of the implant planting hole 300.

In addition, since the bone powder guide groove 115 is recessed while crossing the compression screw thread part 111, the compression screw thread part 111 partially disperses the pressure applied to the lateral side toward the inner wall surface of the implant planting hole 300. Accordingly, it can reduce a patient's pain.

Figure 6:
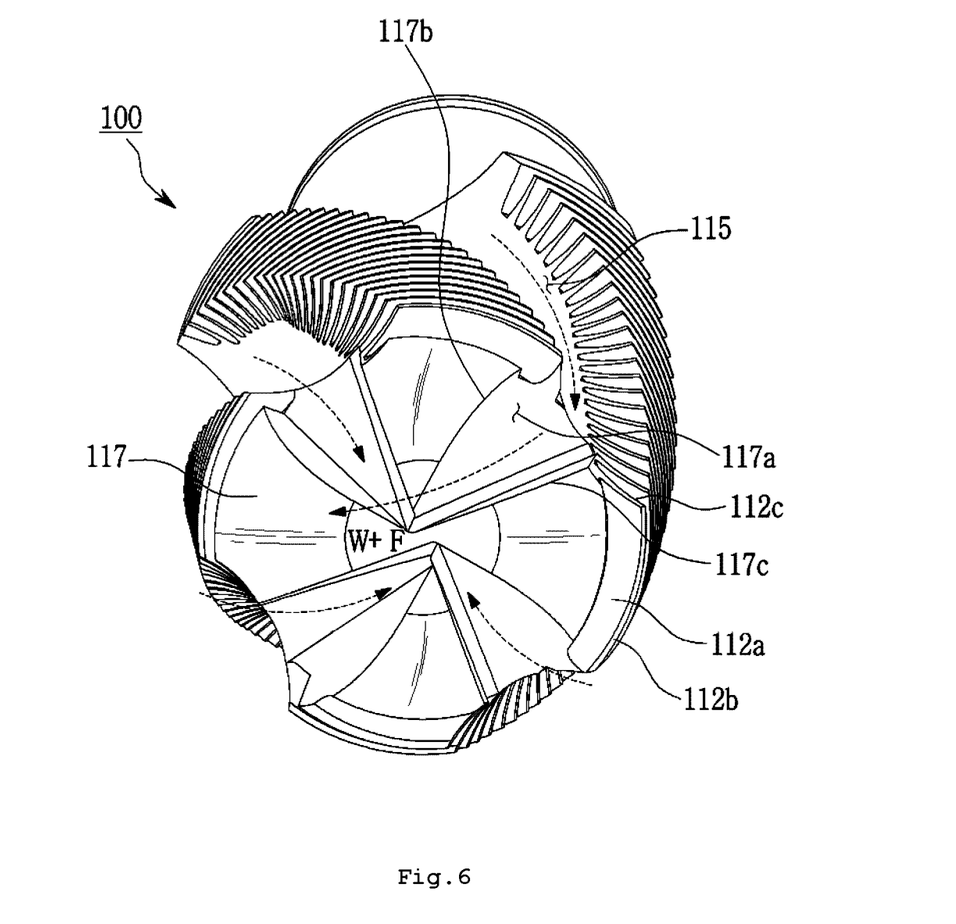
FIG. 6 is a perspective view illustrating a structure of a lower dome of the main body of the condensing screw according to the embodiment of the present invention.

FIG. 6 is an enlarged perspective view of the lower compression dome 117 of the screw main body 110. As illustrated in the drawing, the lower compression dome 117 is formed in a dome shape which is convexly formed on the lower part of the screw main body 110 downwards. The surface of the lower compression dome 117 has a smooth curved surface with a smooth curvature. Accordingly, when maxillary sinus lift is performed, the membrane is not damaged.

A guide groove connection groove 117a radically connected to the bone powder guide groove 115 from the center is formed on the lower compression dome 117. The guide groove connection groove 117a is connected to the bone powder guide groove 115 to move the bone powder (F) and the water (W) transferred through the bone powder guide groove 115 to the inside of the implant planting hole 300 to perform osseodensification.

Since four bone powder guide grooves 115 are formed in a preferred embodiment of the present invention, four guide groove connection grooves 117a are formed in the lower compression dome 117.

Angles of both sides of each guide groove connection groove 117a connected with the bone powder guide groove 115 are different from each other. Based on the rotational direction of the screw main body 110, a guide curved surface 117b having a smooth curved surface is formed in the forward rotational direction, and a vertical surface 117c having a vertical angle is formed in the reverse rotational direction of the screw main body 110.

The guide curved surface 117b is formed as a smooth inclined curved surface in the range of 5 to 60 degrees and is connected to the guide groove connection groove 117a. The guide curved surface 117b is formed in the forward rotational direction of the screw main body 110 in order to prevent damage to the membrane when performing maxillary sinus lift. When the vertical surface 117c having a vertical angle is formed in the forward rotational direction, the vertical surface can tear the membrane while the vertical surface 117c is first in contact with the membrane.

The guide curved surface 117b has the vertical angle to guides the bone powder (F) and the water (W) moved along the bone powder guide groove 115 downward from the lower compression dome 117 when the screw main body 110 is rotated by a gentle angle.

The vertical surface 117c has an angle close to a vertical direction with respect to the surface of the lower compression dome 117 to prevent the bone powder (F), which is moved to the lower part of the lower compression dome 117 by the guide curved surface 117b when the screw main body 110 rotates, from being separated or transferred in the reverse direction.

Moreover, the vertical surface 117c has the vertical angle so that the curved shape of the surface of the lower compression dome 117 can be maximally secured.

Figure 7:
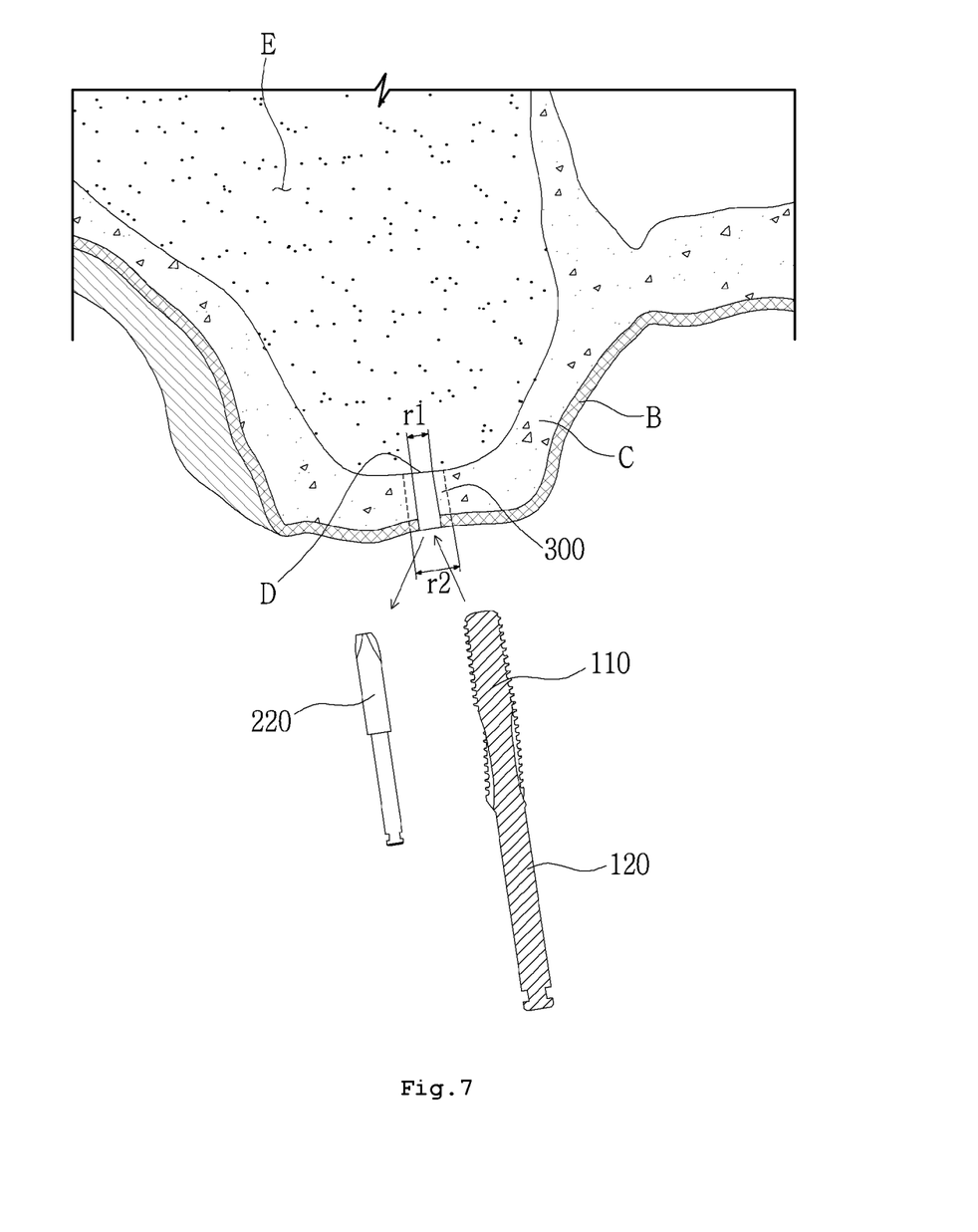
FIGS. 7 and 8 are views illustrating a process of performing maxillary sinus lift using the condensing screw according to the embodiment of the present invention.
Figure 8:
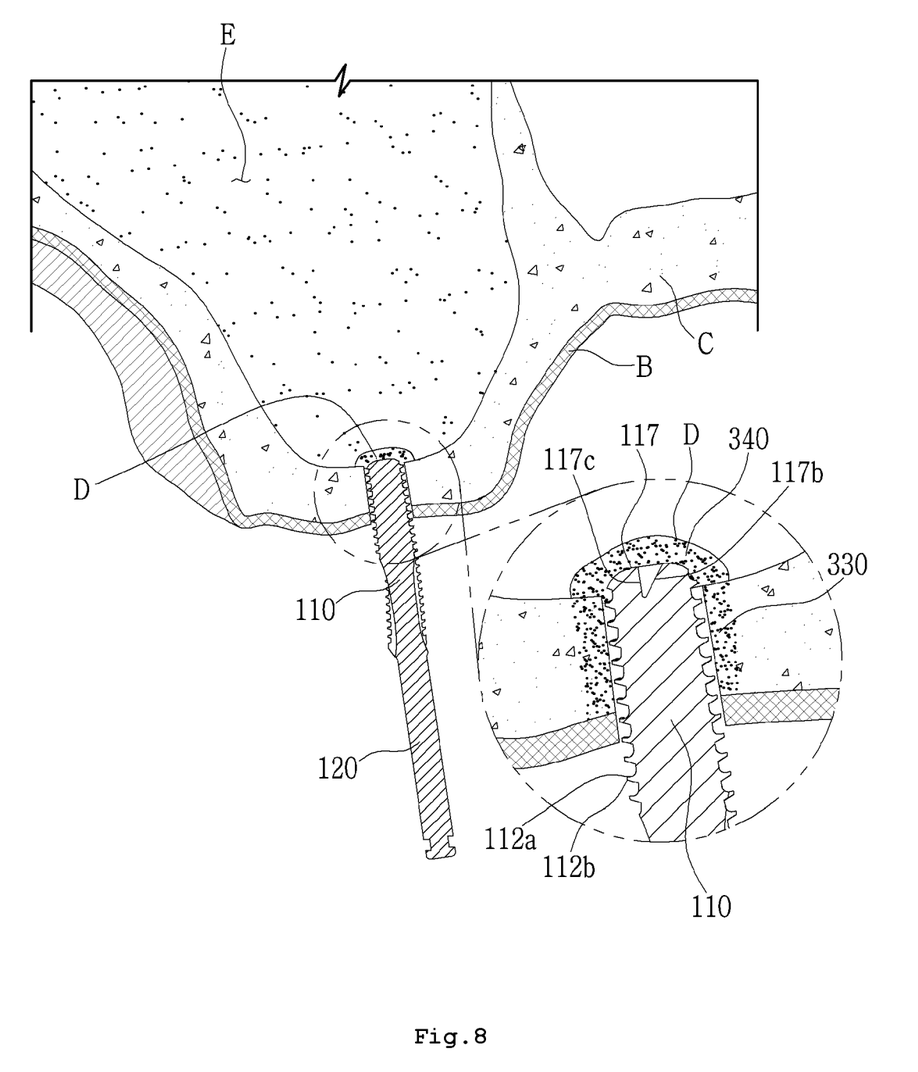

Now, a process of performing implant surgery using the condensing screw 100 according to the present invention will be described. FIGS. 7 and 8 are diagrams illustrating a process of performing maxillary sinus lift on the maxillary molar region by using the condensing screw 100 according to the present invention.

As illustrated in FIG. 7, the operator cuts the gum (B) and performs reaming and osseodensification by using the pilot drill 220, leaving the alveolar bone 113 in the range of 0.5 mm to 1 mm. In this instance, the diameter of the implant planting hole 300 is expanded from an initial diameter (r1) to a final diameter (r2) in order to plant the fixture of the implant. In this instance, a membrane (D) is covered between the maxillary sinus (E) and the alveolar bone 113.

The operator inserts the lower compression dome 117 of the condensing screw 100 into the implant planting hole 300 and drives the driving unit 210. As illustrated in FIG. 2, water (W) is supplied using a water supply member 200. The water (W) is moved along the bone powder guide groove 115 of the screw main body 110.

As illustrated in FIG. 4, when the screw main body 110 is rotated in the clockwise direction, the cutting blade 112a formed in the counterclockwise direction of the compression screw thread 111 of the screw main body 110 comes into line contact with the inner wall surface of the implant planting hole 300, and cuts the inner wall surface of the implant planting hole 300 with cutting force corresponding to the lead angle.

The bone powder (F) cut by the cutting blade 112a is moved along the valley 113 outwards in the radial direction of the screw main body 110, and some of the bone powder is moved to the bone powder guide groove 115 formed to communicate with the valley 113. In this instance, the bone powder (F) is stirred with the water (W) supplied through the bone powder guide groove 115 and moved.

The densification surface 112b and the cutting blade 112a get in surface contact with the inner wall surface of the implant planting hole 300 to compress the bone powder (F) moved through the valley 113. The bone powder (F) is continuously in contact with the densification surface 112b by the rotation of the screw main body 110, receives pressure to perform and the pressure is applied to perform osseodensification.

The screw main body 110 is gradually inserted into the upper part of the implant planting hole 300 so that the implant planting hole 300 is gradually expanded the lateral osseodensification region 330 of a predetermined thickness is formed on the inner wall surface.

Meanwhile, the bone powder (F) and the water (W) moved along the bone powder guide groove 115 and water are moved to the upper surface of the lower compression dome 117 through the guide curved surface 117b of the guide groove connection groove 117a. When the screw main body 110 rotates and is moved to the upper part of the implant planting hole 300, the bone powder (F) and the water (W) moved to the upper part of the lower compression dome 117 are gradually compressed upwards.

Furthermore, as illustrated in FIG. 8, while the membrane (D) is lifted, the bone powder (F) and the water are compressed between the alveolar bone 113 and the membrane (D) so that the upper osseodensification region 340 is formed. The lower compression dome 117 has a smoothly curved surface, thereby lifting the membrane (D) without any damage.

Because also the upper osseodensification region 340 has a sufficient thickness by the bone powder (F) and the water (W) transferred along the bone powder guide groove 115, the implant can be planted without an additional osseodensification process.

The operator plants the fixture (not shown) of the implant into the implant planting hole 300 after separating the screw main body 110 to the outside, and sequentially assembles an abutment (not shown) and a crown (not shown) to finish the implant surgery.

Figure 9:
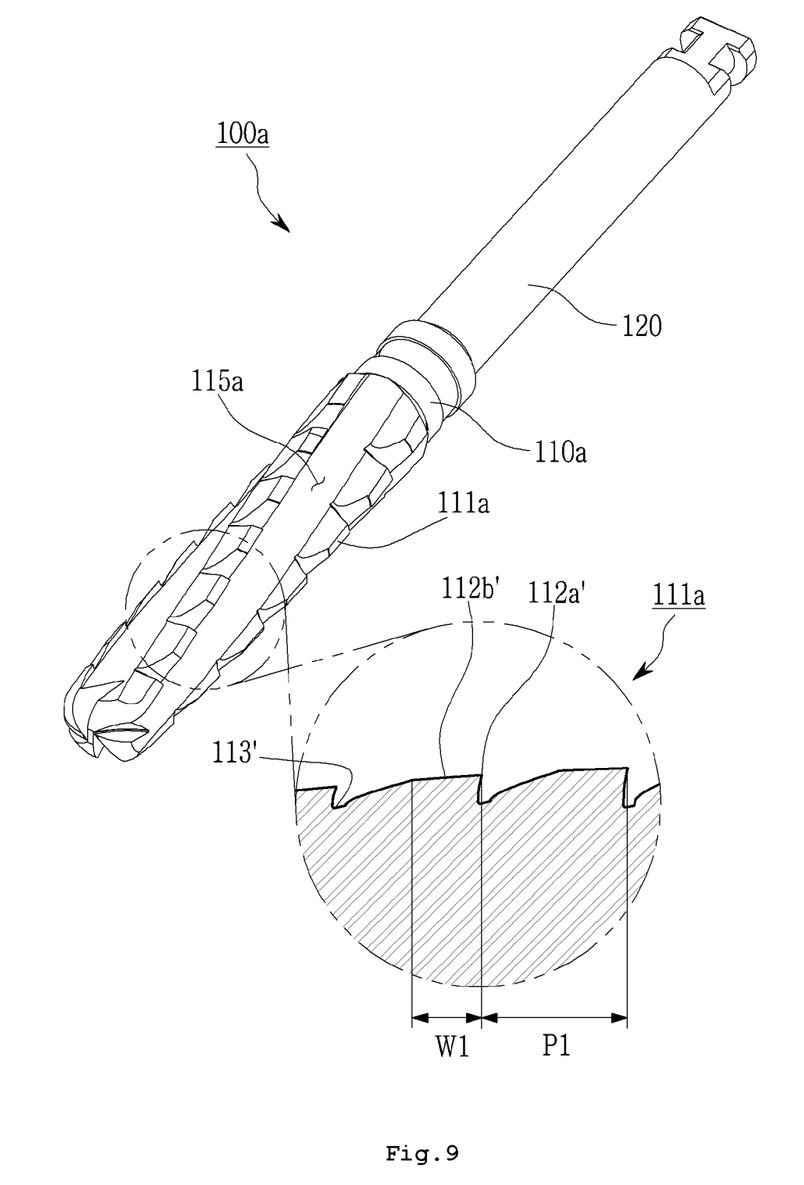
FIG. 9 is a perspective view illustrating a condensing screw according to another embodiment of the present invention.

FIG. 9 is a perspective view illustrating the configuration of a condensing screw 100a according to another embodiment of the present invention.

The condensing screw 100a according to the second embodiment of the present invention has a bone powder guide groove 115a of the screw main body 110a which is wider than the bone powder guide groove 115 of the condensing screw 100. Additionally, a pitch (P1) of the compression screw thread part 111a is widely formed. In addition, the width (W1) of a densification surface 112b' forming a thread is also widely formed.

Accordingly, since a contact area between the inner wall surface of the implant planting hole 300 and the condensing screw 100a is further increased, the osseodensification process can be more easily performed, and the transfer of the bone powder (F) and the water (W) can be more smoothly performed.

As described above, the condensing screw for implant surgery according to the present invention has the compression screw thread part formed with a close pitch in the opposite direction to the rotational direction of the screw main body, and the bone powder guide groove formed between the compression screw thread parts to be overlapped.

The compression screw thread part is provided to perform expansion through cutting by getting in contact with the inner wall surface of the implant planting hole to press the inner wall surface of the implant planting hole when the screw main body is rotated and to perform osseodensification by laterally pressing the bone powder generated during cutting.

At the same time, the bone powder is supplied to the lower compression dome of the screw main body through the bone powder guide groove to form an osseodensification process region inside the implant planting hole. So, the membrane can be lifted without damaging the membrane of the maxillary sinus. In addition, the osseodensification process region is formed at the lower portion of the membrane, thereby enabling implant placement without an additional osseodensification process.

The conventional method performs processes of drilling using a number of drills to gradually increase the diameter after drilling using the pilot drill to plant the conventional implant, performing osseodensification process if necessary, performing final drilling, and planting an implant. However, the condensing screw according to the present invention can simultaneously perform drilling a hole using the pilot drill, expansion and osseodensification process using the condensing screw, thereby shortening a process of implant placement.

Moreover, since the implant placement process is shortened, the burden of the operator can be reduced.

The technical idea of the present invention has been described through several embodiments.

It is to be appreciated that those skilled in the art can change or modify the embodiments from the above description in various ways. Although it is not clearly illustrated or described herein, it is to be appreciated that those skilled in the art can change or modify the embodiments from the above description in various ways without departing from the scope and spirit of the present invention and such changes and modifications belong to the scope of the present invention. While the present invention has been described with reference to the particular illustrative embodiments, it is not to be restricted by the embodiments but only by the appended claims.

What is claimed is:

1. A condensing screw for planting an implant comprising:
 a screw main body which is inserted into an implant planting hole formed by a pilot drill to enlarge the implant planting hole to a size that an implant fixture can be inserted into the implant planting hole, and which forms osseodensification regions on a lateral surface and an inner wall surface of the implant planting hole; and
 a shank extending from an upper part of the screw main body (110), the shank being configured to be coupled to a driving unit and transmitting rotational force of the driving unit to the screw main body, wherein the screw main body comprises:
  a compression screw thread part spirally formed on the surface of the screw main body in the opposite direction to a rotational direction of the screw main body to provide a cutting force in the insertion direction when the screw main body is rotated, and compressing bone powder by laterally pressing the inner wall surface of the implant planting hole; and
  a plurality of bone powder guide grooves formed to be spirally recessed in the opposite direction to the rotational direction of the screw main body at regular intervals along the outer circumference of the screw main body to the upper part from an lower part of the screw main body in order to guide the bone powder separated from the inner wall surface of the implant planting hole and water supplied from an outside to the lower part of the screw main body by the cutting force of the compression screw thread part.

2. The condensing screw according to claim 1, wherein the plurality of bone powder guide grooves are formed to have a pitch larger than the length of the screw main body so that the plurality of bone powder guide grooves can be independently provided in a longitudinal direction of the screw main body.

3. The condensing screw according to claim 2, wherein the compression screw thread part is formed to have a pitch smaller than the pitch of the bone powder guide grooves so that threads and valleys are repeated multiple times spirally in the longitudinal direction of the screw main body.

4. The condensing screw according to claim 3, wherein a densification surface (112b) of a predetermined area is formed on an upper part of the thread to get in surface contact with the inner wall surface of the implant planting hole to compress the bone powder, and a cutting blade (112a) is disposed at the front end of the thread to get in line contact with the inner wall surface of the implant planting hole to form cutting force.

5. The condensing screw according to claim 4, wherein the screw main body includes a lower compression dome disposed at the lower part of the screw main body and having a convex curved surface, wherein the lower compression dome includes a plurality of guide groove connection grooves connected to the bone powder guide grooves to be radially recessed on the basis of the center, and wherein each guide groove connection groove has a guide curved surface slantly connected to the bone powder guide grooves in the forward rotational direction based on the rotational direction of the screw main body, and a vertical surface formed vertically to the bone powder guide groove in the reverse rotational direction to the rotational direction.

* * * * *